US012388961B2

(12) United States Patent
Philipp et al.

(10) Patent No.: US 12,388,961 B2
(45) Date of Patent: Aug. 12, 2025

(54) FEEDBACK SYSTEMS FOR OPTIMIZED DISPLAY OPERATION

(71) Applicant: GM GLOBAL TECHNOLOGY OPERATIONS LLC, Detroit, MI (US)

(72) Inventors: Tzvi Philipp, Bet Shemesh (IL); Manoj Kumar Sharma, Troy, MI (US); Joseph F. Szczerba, Grand Blanc, MI (US); Thomas A. Seder, Fraser, MI (US)

(73) Assignee: GM GLOBAL TECHNOLOGY OPERATIONS LLC, Detroit, MI (US)

( * ) Notice: Subject to any disclaimer, the term of this patent is extended or adjusted under 35 U.S.C. 154(b) by 66 days.

(21) Appl. No.: 18/492,117

(22) Filed: Oct. 23, 2023

(65) Prior Publication Data

US 2025/0133191 A1 Apr. 24, 2025

(51) Int. Cl.
*H04N 9/31* (2006.01)
*A61B 5/00* (2006.01)
*B60Q 9/00* (2006.01)
*G06F 3/01* (2006.01)
*A61B 5/024* (2006.01)
*B60N 2/00* (2006.01)

(52) U.S. Cl.
CPC ............. *H04N 9/31* (2013.01); *A61B 5/6893* (2013.01); *B60Q 9/00* (2013.01); *G06F 3/012* (2013.01); *G06F 3/013* (2013.01); *A61B 5/024* (2013.01); *B60N 2/0022* (2023.08)

(58) Field of Classification Search
CPC ......... A61B 5/024; A61B 5/02; A61B 5/6893; G06F 3/012; G06F 3/013; H04N 9/31; B60Q 9/00; B60N 2/0022

USPC .................. 348/744; 382/103, 115, 117, 118
See application file for complete search history.

(56) References Cited

U.S. PATENT DOCUMENTS

| 2010/0070988 | A1 | 3/2010 | Cohen et al. |
| 2013/0300637 | A1* | 11/2013 | Smits ..................... G02B 30/26 345/8 |
| 2019/0278091 | A1* | 9/2019 | Smits ..................... G03B 35/18 |

FOREIGN PATENT DOCUMENTS

DE 102013203653 A1 9/2014

OTHER PUBLICATIONS

German Office Action from counterpart DE1020231358820, dated Sep. 24, 2024.

* cited by examiner

*Primary Examiner* — Sherrie Hsia (57) ABSTRACT

A system includes a projector module configured to project a visual media for a user, a user tracking sensor configured to sense whether the user is observing the visual media, and a control module configured to detect whether the user is looking at the projector module based on the user tracking sensor, in response to detecting the user is looking at the projector module, control the projector module to initiate projecting of the visual media for the user, detect an interruption of the user observing the visual media based on the user tracking sensor, and in response to detecting the interruption of the user observing the visual media, control the projector module to pause projecting of the visual media for the user. Other example systems and methods for controlling projection of a visual media for a user in a vehicle are also disclosed.

20 Claims, 7 Drawing Sheets

FEEDBACK SYSTEMS FOR OPTIMIZED DISPLAY OPERATION

INTRODUCTION

The information provided in this section is for the purpose of generally presenting the context of the disclosure. Work of the presently named inventors, to the extent it is described in this section, as well as aspects of the description that may not otherwise qualify as prior art at the time of filing, are neither expressly nor impliedly admitted as prior art against the present disclosure.

The present disclosure relates to feedback systems for optimized display operation.

Vehicles are often employed in ride sharing scenarios. In such examples, sometimes multiple passengers share the same vehicle, including the same passenger space (e.g., a rear passenger space) for the duration of a trip. In some cases, the ride sharing vehicle may have an interactive display system, such as a virtual display system to provide information, entertainment, etc. for the passengers.

SUMMARY

A system for controlling projection of a visual media for a user in a vehicle includes a projector module configured to project a visual media for a user in the vehicle, a user tracking sensor configured to sense whether the user is observing the visual media, and a control module in communication with the projector module and the user tracking sensor. The control module is configured to detect whether the user is looking at the projector module based on a first signal from the user tracking sensor, in response to detecting the user is looking at the projector module, control the projector module to initiate projecting of the visual media for the user, detect an interruption of the user observing the visual media based on a second signal from the user tracking sensor, and in response to detecting the interruption of the user observing the visual media, control the projector module to pause projecting of the visual media for the user.

In other features, the user tracking sensor includes at least one of an eye tracking sensor and a face tracking sensor.

In other features, the system further includes an occupancy detection sensor configured to sense a parameter associated with a seat in the vehicle, the control module is in communication with the occupancy detection sensor, and the control module is configured to detect whether the seat is occupied by an object indicative of an individual based on the sensed parameter, and control the projector module to initiate projecting of the visual media for the user in response to detecting that the seat is occupied by the object indicative of the individual.

In other features, the occupancy detection sensor includes at least one of a biometric sensor positioned in the seat and a weight sensor positioned in the seat.

In other features, the projector module includes a retinal projector module configured to project the visual media directly into retinas of the user in the vehicle.

In other features, the control module is configured to generate an alert for the user in response to detecting the interruption.

In other features, the alert includes at least one of an audible alert and a haptic alert.

In other features, the control module is configured to detect the user looking again at the projector module after the interruption and control the projector module to reinitiate the projecting of the visual media for the user in response to detecting the user looking again at the projector module after the interruption.

In other features, the control module is configured to control the projector module to reinitiate the projecting of the visual media at a point of interruption in the visual media.

In other features, the control module is configured to detect the user looking again at the projector module after the interruption, determine a period of time between detecting the interruption of the user observing the visual media and detecting the user looking again at the projector module after the interruption, and control the projector module to pause projecting of the visual media for the user only if the period of time is greater than a defined threshold.

In other features, a vehicle includes the system, a first seat, and a second seat opposing the first seat, and the projector module is positioned in the first seat and configured to project the visual media towards the second seat.

In other features, the user tracking sensor is positioned in the first seat and coaligned with the projector module.

A method for controlling projection of a visual media for a user in a vehicle includes detecting whether the user is looking at a projector module based on a first signal received from a user tracking sensor, in response to detecting the user is looking at the projector module, controlling the projector module to initiate projecting of the visual media for the user, detecting an interruption of the user observing the visual media based on a second signal from the user tracking sensor, and in response to detecting the interruption of the user observing the visual media, controlling the projector module to pause projecting of the visual media for the user.

In other features, the method further includes detecting whether a seat is occupied by an object indicative of an individual based on a sensed parameter received from an occupancy detection sensor.

In other features, controlling the projector module to initiate projecting of the visual media for the user includes controlling the projector module to initiate projecting of the visual media in response to detecting that the seat is occupied by the object indicative of the individual.

In other features, the user tracking sensor includes at least one of an eye tracking sensor and a face tracking sensor, and the occupancy detection sensor includes at least one of a biometric sensor positioned in the seat and a weight sensor positioned in the seat.

In other features, the method further includes generating an alert for the user in response to detecting the interruption.

In other features, the alert includes at least one of an audible alert and a haptic alert.

In other features, the method further includes detecting the user looking again at the projector module after the interruption, and controlling the projector module to reinitiate the projecting of the visual media for the user in response to detecting the user looking again at the projector module after the interruption.

In other features, controlling the projector module to reinitiate the projecting of the visual media for the user includes controlling the projector module to reinitiate the projecting of the visual media at a point of interruption in the visual media.

In other features, the method further includes detecting the user looking again at the projector module after the interruption, and determining a period of time between detecting the interruption of the user observing the visual media and detecting the user looking again at the projector module after the interruption.

In other features, controlling the projector module to pause projecting of the visual media includes controlling the projector module to pause projecting of the visual media only if the period of time is greater than a defined threshold.

Further areas of applicability of the present disclosure will become apparent from the detailed description, the claims and the drawings. The detailed description and specific examples are intended for purposes of illustration only and are not intended to limit the scope of the disclosure.

BRIEF DESCRIPTION OF THE DRAWINGS

The present disclosure will become more fully understood from the detailed description and the accompanying drawings, wherein.

DETAILED DESCRIPTION

In ride sharing scenarios, multiple passengers in a vehicle may share the same passenger space for the duration of a trip. Sometimes, such ride sharing vehicles may have an interactive display system (e.g., a virtual display system) for the passengers. In some cases, a display of one occupant may be blocked by another occupant and/or an object due to the location of the occupants and/or the object, during entry and/or exit of the vehicle, etc. The blocking of the display may interrupt the occupant's capability to view and/or interact with the display system.

The systems according to the present disclosure enable the detection of display blockages and then the subsequent control of the display in response to the obstruction to reengage with the viewer. As a result, the inconvenience of the interruption for the viewer may be reduced and, in some cases, minimized.

Figure 1:
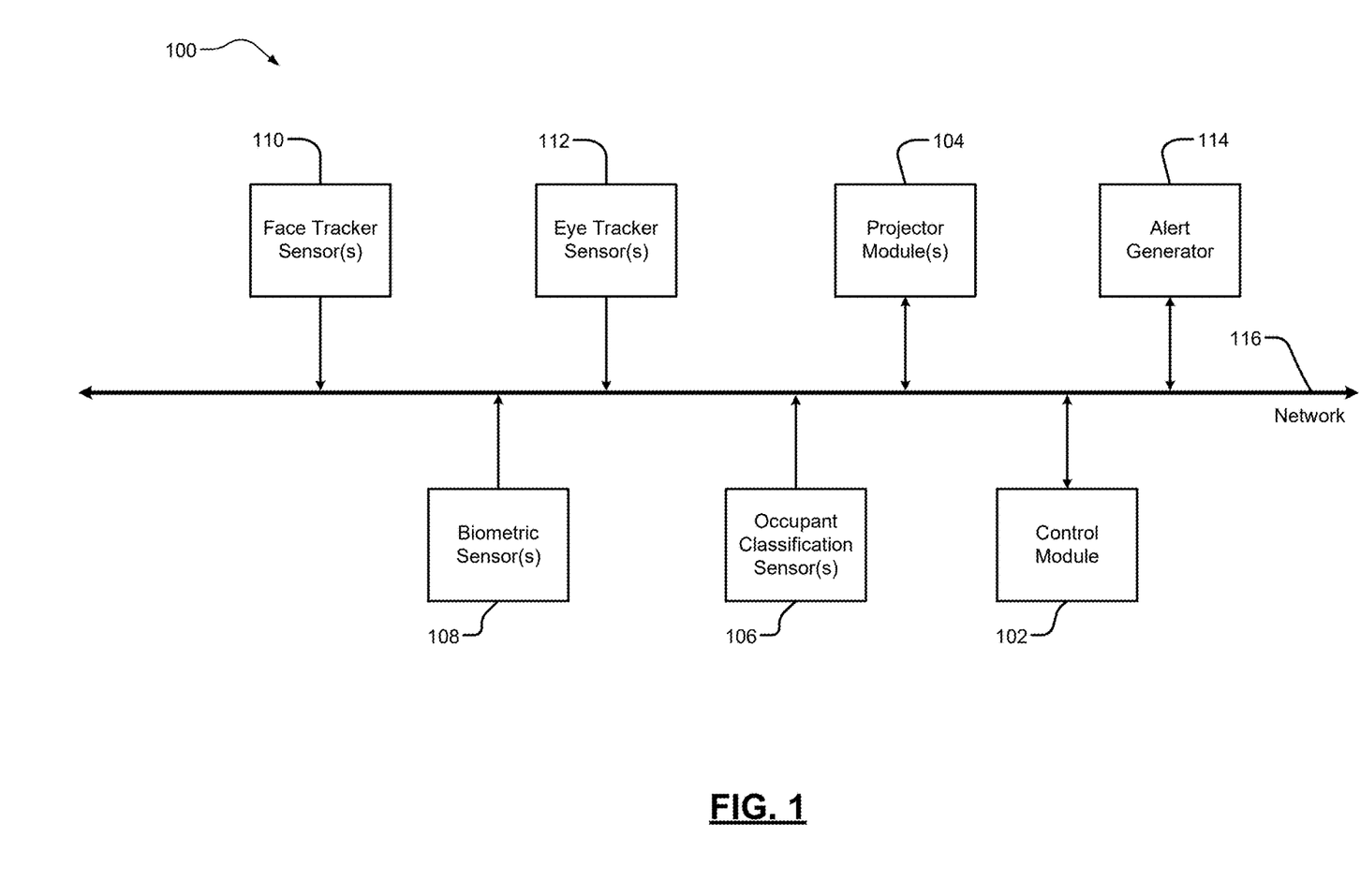
FIG. 1 is a functional block diagram of an example system for controlling projection of visual media for occupants, according to the present disclosure.

Referring now to FIG. 1, a block diagram of an example system 100 is presented for controlling projection of a visual media for a user (e.g., an occupant, a viewer, a passenger, etc.) in a vehicle. As shown in FIG. 1, the system 100 generally includes a control module 102, various sensors, one or more projector modules 104, and an optional alert generator 114. In the example of FIG. 1, the sensors may include one or more user tracking sensors (e.g., a face tracker sensor 110, an eye tracker sensor 112, etc.) and/or one or more occupancy detection sensors (e.g., an occupant classification sensor 106, a biometric sensor 108, etc.). In various embodiments, the system 100 may include two or more occupant classification sensors 106, two or more biometric sensors 108, two or more face tracker sensors 110 and two or more eye tracker sensors 112.

Although FIG. 1 illustrates the system 100 as including specific modules, it should be appreciated that one or more other modules may be employed if desired. Additionally, while the system 100 is shown as including multiple separate modules, any combination of the modules and/or the functionality thereof may be integrated into one or more modules. Further, although the system 100 of FIG. 1 is shown as including particular sensors, it should be appreciated that the system 100 and/or other systems may include more or less sensors, sensors having different functionalities, etc.

In various embodiments, the modules and sensors of the system 100 may be in communication with each other and may share parameters via a network 116, such as a controller (or car) area network (CAN). In such examples, the parameters may be shared via one or more data buses of the network 116. As such, various parameters may be made available by a given module and/or sensor to other modules and/or sensors via the network 116.

Figure 2:
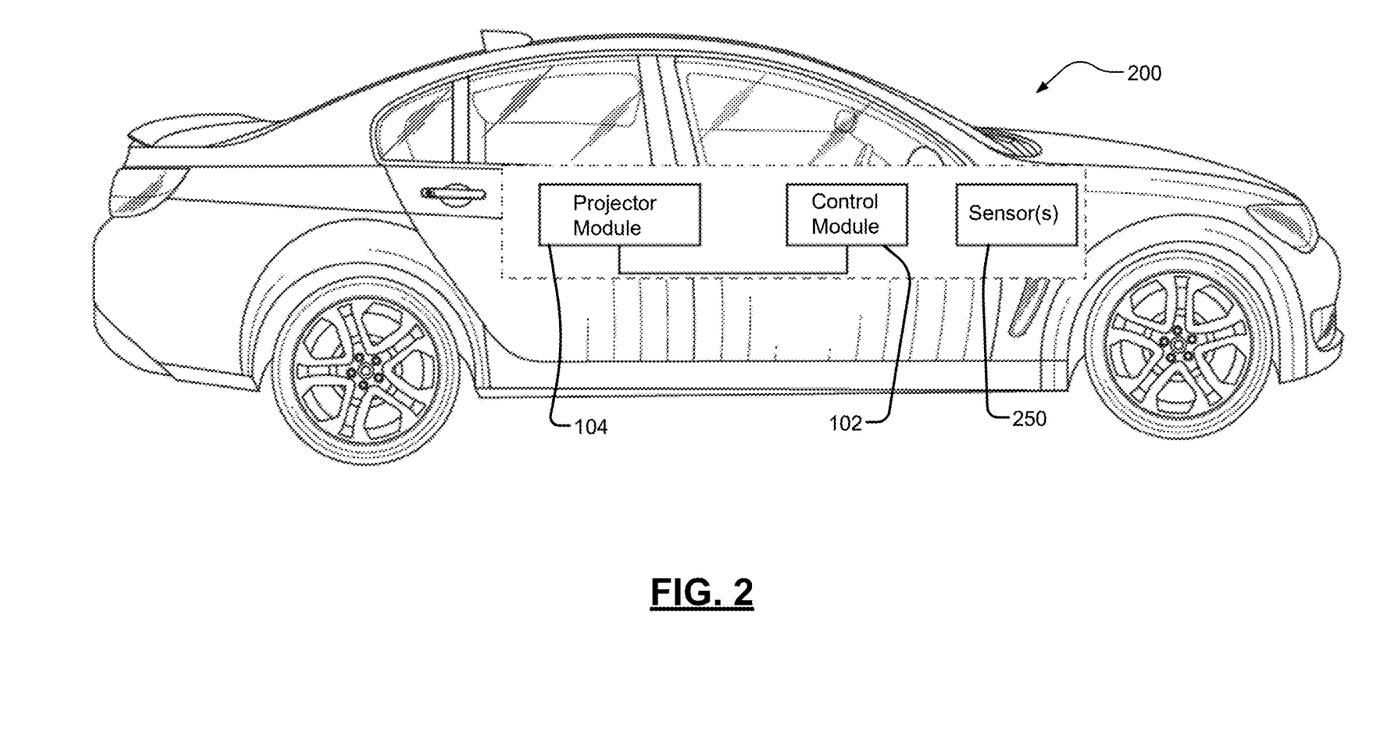
FIG. 2 is a vehicle including portions of the system of FIG. 1, according to the present disclosure.

The system 100 of FIG. 1 may be employable in any suitable vehicle, such as an electric vehicle (e.g., a pure electric vehicle, a plug-in hybrid electric vehicle, etc.), an internal combustion engine vehicle, etc. Additionally, the system 100 may be applicable to an autonomous vehicle, a semi-autonomous vehicle, etc. For example, FIG. 2 depicts a vehicle 200 including the control module 102 and the projector module 104 of FIG. 1, and one or more sensors 250 (e.g., the occupant classification sensor 106, the heart rate sensor 108, the face tracker sensor 110, the eye tracker sensor 112, etc.) in communication with the control module 102 and/or the projector module 104. While the system 100 is generally described relative to a vehicle (e.g., the vehicle 200), it should be appreciated that the system 100 may be implemented with other suitable applications, such as other modes of transportation (e.g., a plane, a train, etc.), in rooms (e.g., a waiting room, etc.), etc.

In various embodiments, a ride share vehicle (e.g., the vehicle 200) may allow multiple passengers the ability to share the same passenger space for a period of time. In some examples, not all passengers will enter and exit the vehicle at the same time. This often creates a scenario where one or more passengers entering and/or exiting the vehicle may interfere with the viewing of visual media (e.g., via an infotainment system as further explained below) for other passengers during the boarding and disembarking of the vehicle.

Figure 3:
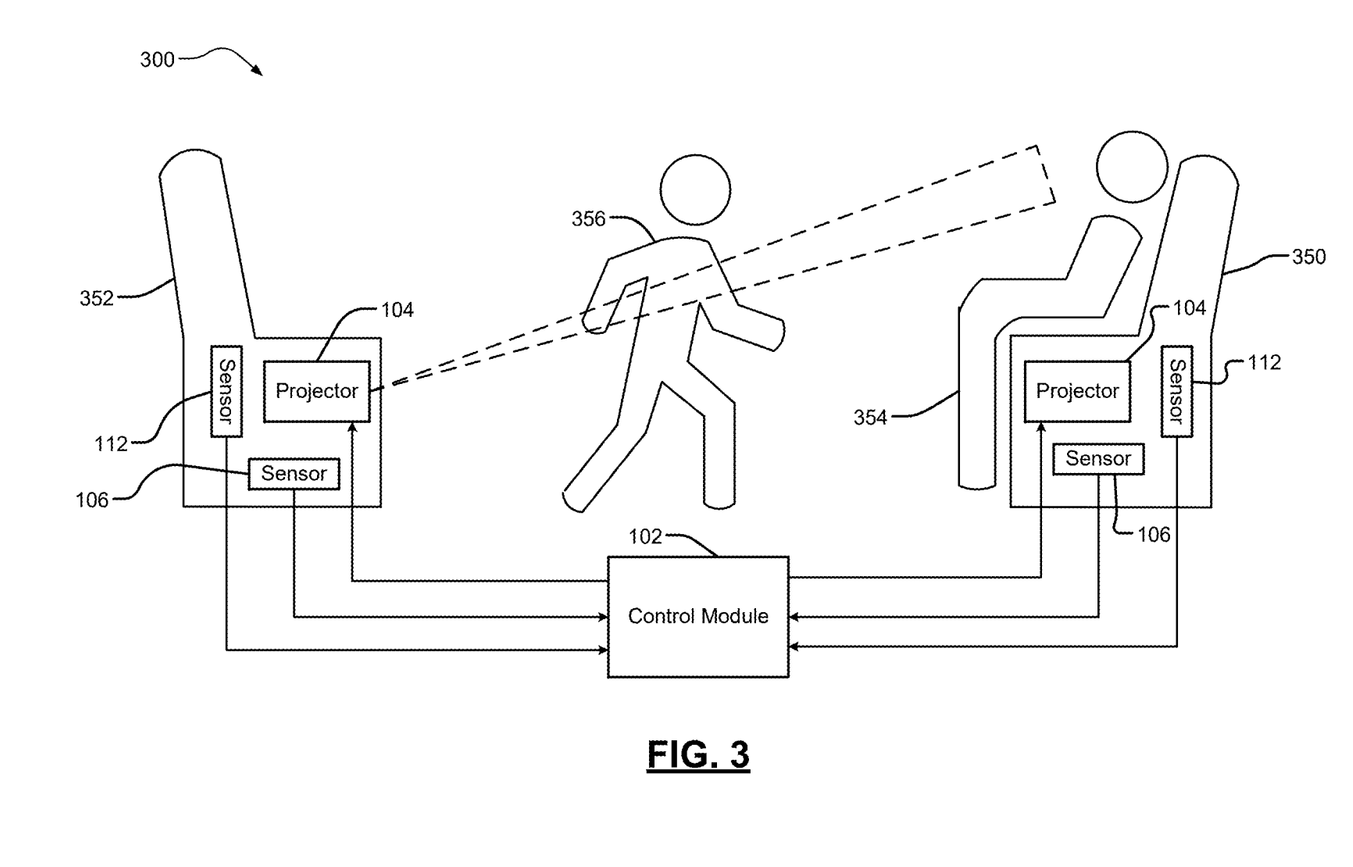
FIG. 3 is a functional block diagram of an example system in a vehicle where a disembarking occupant interrupts another occupant from viewing visual media, according to the present disclosure.

For example, FIG. 3 depicts a system 300 of a vehicle in which such a scenario exists. As shown, the system 300 includes two opposing seats 350, 352, an occupant (e.g., a passenger, a user, etc.) 354 located in the seat 350, and another occupant 356 disembarking from the vehicle. The system 300 further includes the control module 102, multiple sets of sensors 106, 112, and two projector modules 104 of FIG. 1. As shown in FIG. 3, the disembarking occupant 356 interrupts the occupant 354 from viewing visual media output from one of the projector modules 104.

In other examples, one or more physical objects may interfere with the viewing of visual media (e.g., via the infotainment system) for other passengers. For example, an occupant may place a personal item (e.g., a bag, luggage, a parcel, an animal, etc.) on an unoccupied seat and in the viewing area of another fellow occupant in the vehicle.

Figure 4:
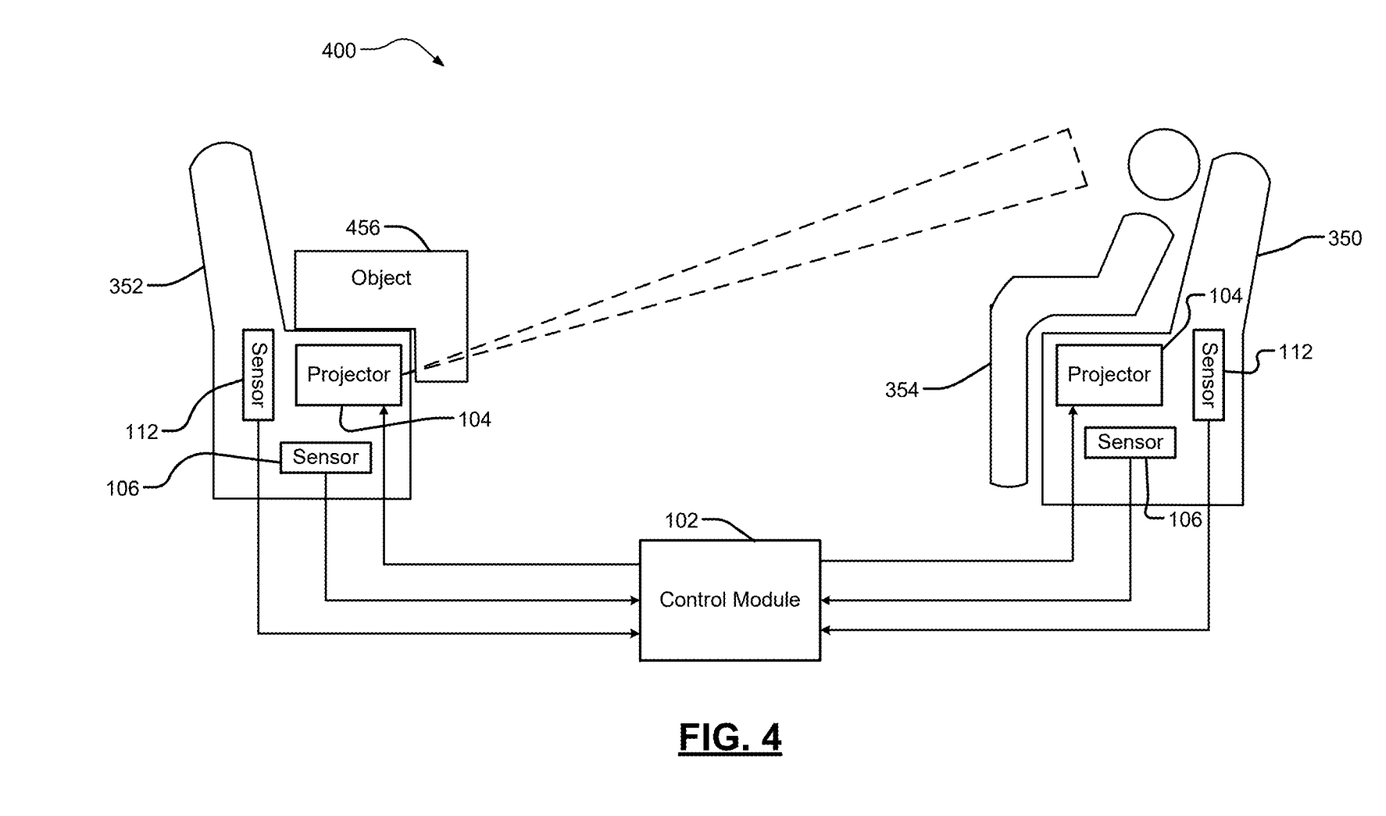
FIG. 4 is a functional block diagram of an example system in a vehicle where an object on a seat interrupts an occupant from viewing visual media, according to the present disclosure.

FIG. 4 depicts a system 400 of a vehicle in which such a scenario exists. As shown, the system 400 includes the opposing seats 350, 352 of FIG. 3, the occupant 354 of FIG.

3 located in the seat 350, and an object 456 positioned on the seat 352. The system 400 further includes the control module 102, the sets of sensors 106, 112, and the projector modules 104 of FIG. 3. As shown in FIG. 4, the object 456 interrupts the occupant 354 from viewing visual media output from one of the projector modules 104.

In the example of FIGS. 3-4, one set of the sensors 106, 112 and one of the projector module 104 are positioned in each seat 350, 352. With this arrangement, the projector module 104 and the eye tracker sensor 112 may be coaligned so that the projector module 104 and the eye tracker sensor 112 have same perspective for the occupant 354. In other examples, any one of the sensors 106, 112 and/or the projector modules 104 may be positioned at another suitable location in the vehicle. For example, one of the projector modules 104 may be positioned on a wall of the vehicle opposing the occupant 354 and/or another suitable location that is generally in a straight line with the occupant 354. Additionally, the eye tracker sensor 112 may be offset from the projector module 104 and/or positioned in another suitable area of vehicle if desired so as the eye tracker sensor 112 is able to observe the eye(s) of the occupant 354.

Further, while the systems 300, 400 of FIGS. 3-4 are shown as including the occupant classification sensor 106 and the eye tracker sensors 112, it should be apparent other suitable user tracking sensors (e.g., the face tracker sensor 110, etc.) and/or other suitable occupancy detection sensors (e.g., the biometric sensor 108, etc.) may be employed if desired.

Figure 5:
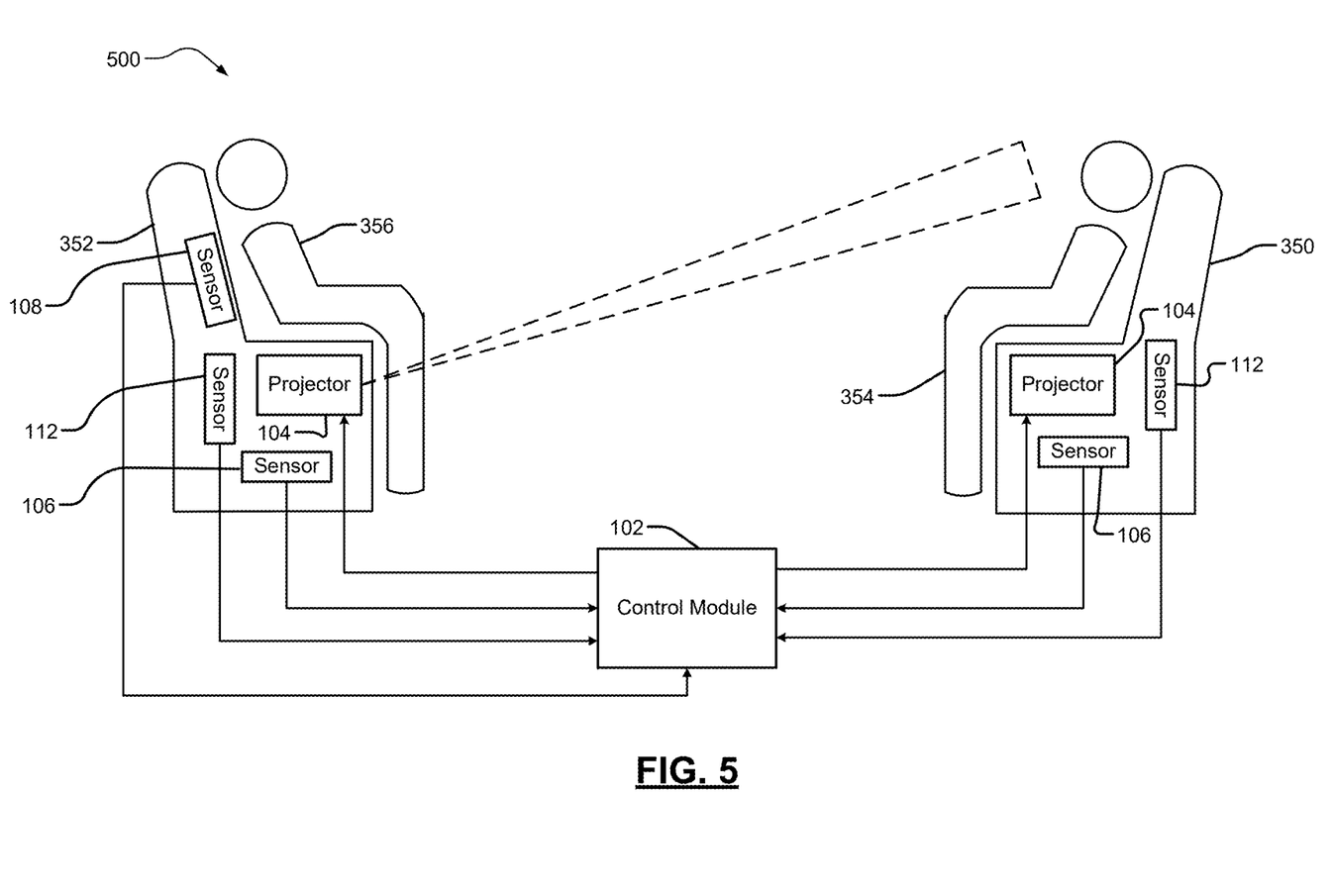
FIG. 5 is a functional block diagram of an example system in a vehicle where a seated occupant interrupts another occupant from viewing visual media, according to the present disclosure.

For example, FIG. 5 depicts a system 500 substantially similar to the systems 300, 400 of FIGS. 3-4, but where the system 500 includes a biometric sensor 108. In the example of FIG. 5, the system 500 also includes the opposing seats 350, 352 of FIG. 3 occupied by the occupants 354, 356, respectively, the control module 102, the sets of sensors 106, 112, and the projector modules 104 of FIG. 3. As shown in FIG. 5, the occupant 356 interrupts the occupant 354 from viewing visual media output from one of the projector modules 104.

With continued reference to FIG. 1, a ride share vehicle may offer individualized or collective infotainment features for users in the vehicle. Such infotainment features are generally implemented with a projection-based system, such as the projector module 104. For example, the projector module 104 of FIG. 1 generally projects visual media for an occupant in the vehicle, as referenced herein. For instance, when the projector module 104 is located in a seat (e.g., the seat 352 of FIGS. 3-5), the projector module 104 can project the visual media towards an opposing seat (e.g., the seat 350 of FIGS. 3-5) and/or an occupant in the opposing seat.

In various embodiments, the projector module 104 may be any suitable device for projecting visual media. For example, the projector module 104 may provide the occupant a virtual reality display that is physically projected directly into the occupant's pupil. In such examples, the projector module 104 may include a retinal projector module to project the visual media directly into one or both retinas of the occupant. In this example, the retinas may function as the display. In other examples, the projector module 104 may rely on an external display. For example, the projector module 104 may project the visual media on an intermediate display, such as an optical element (e.g., a diffuser, etc.).

The alert generator 114 of FIG. 1 generally controls activation of one or more alerts to notify one or more occupants in the vehicle of an interruption. For example, and as further explained herein, the alert generator 114 can generate an alert (e.g., an audible alert, a haptic alert, a visual alert, etc.) for an occupant in response to detecting an interruption.

The occupancy detection sensors of FIG. 1 generally detect or sense a parameter associated with a seat in the vehicle. In this manner, the occupancy detection sensors can assist in detecting whether a seat is occupied. For example, the occupant classification sensor 106 may detect a size and/or shape of an object, a weight of an object, etc. For instance, the occupant classification sensor 106 may be a weight sensor positioned in a seat (e.g., the seat 350 of FIGS. 3-5) for sensing mass. In other examples, the occupant classification sensor 106 may be a camera, a radar sensor, etc. for sensing a size and/or shape of an object. Additionally and/or alternatively, the biometric sensor 108 may be employed to detect whether a seat is occupied. For example, the biometric sensor 108 may be a heart rate sensor, a respiration sensor, and/or another suitable sensor positioned in a seat for detecting a biometric (e.g., a heart rate, breathing, etc.) of an occupant.

The user tracking sensors of FIG. 1 generally detect or sense whether an occupant is observing visual media or looking in the direction of the project module 104. For example, the face tracker sensor 110 may include a camera for tracking movements of the occupant's face. Likewise, the eye tracker sensor 112 may include a camera for tracking the occupant's eye. In various embodiments, the user tracking sensors may be positioned in an opposing seat of the occupant or in another suitable location and/or coaligned with the projector module 104, as explained herein.

In some examples, the user tracking sensors may include other suitable types. For example, location sensors, such as GPS sensors and/or other location data collecting sensors may be employed to track real time positioning of each occupant in the vehicle.

With continued reference to FIG. 1, the control module 102 may detect whether an occupant is looking at the projector module 104. For example, the control module 102 may receive one or more signals from the face tracker sensor 110, the eye tracker sensor 112, and/or another suitable user tracking sensor providing feedback indicating the occupant is gazing towards the projector module 104. Based on the received signal(s), the control module 102 can make a determination as to whether the occupant is looking at the projector module 104.

Then, in response, the control module 102 may control the projector module 104 to initiate projecting of visual media for the occupant. For example, after determining that the occupant is looking at the projector module 104, the control module 102 can transmit a control signal to the projector module 104, thereby instructing the projector module 104 to project the visual media. In such examples, the projector module 104 may project the visual media directly into the occupant's pupil or on an intermediate display, as explained herein.

In some examples, the control module 102 may control various parameters associated with the visual media. For example, the occupant may provide user input to the control module 102 or otherwise interact with the control module 102 via gestures detected by one or more of the user tracking sensors. In such examples, the control module 102 may adjust a volume, adjust an image brightness, adjust content, etc. based on the detected gestures of the occupant.

In various embodiments, the control module 102 may control the projector module 104 to project the visual media for the occupant only if additional conditions apply. For example, the control module 102 may control the projector module 104 to initiate projecting of the visual media in response to detecting that a seat is occupied by an object resembling an individual. For instance, the control module 102 may receive one or more signals with a sensed parameter from the occupant classification sensor 106, the biometric sensor 108, and/or another suitable occupancy detection sensor, and then detect whether a seat is occupied by an object indicative of an individual based on the sensed parameter. For instance, the parameter may include a sensed weight, a detected size, a detected shape, etc. After determining that the seat is occupied by an individual, the control module 102 may transmit the control signal to the projector module 104 to initiate projecting of the visual media.

Additionally, the control module 102 may detect an interruption of the occupant observing the visual media. In such examples, any obscuration of the direct path between the projector module 104 and/or the display and the occupant will disrupt the viewing. For instance, the occupant may not view the visual media because another occupant or object (e.g., the occupant 356 of FIGS. 3 and 5, the object 456 of FIG. 4, etc.) is blocking the projected media, the occupant has looked away, etc. In such scenarios, the control module 102 may receive one or more additional signals from the face tracker sensor 110, the eye tracker sensor 112, and/or another suitable user tracking sensor indicating the occupant is no longer viewing the visual media. In other examples, the control module 102 may receive a signal based on GPS or other location data relative to a destination indicating that an interruption will soon occur (and therefore detected). Then, based on the received signal(s), the control module 102 can detect an interruption of the occupant observing the visual media.

Then, the control module 102 may control the projector module 104 to pause projecting of the visual media for the occupant in response to detecting the interruption. For example, the control module 102 may send a control signal to the projector module 104 pause (e.g., stop projecting, etc.) the visual media so that the occupant may not miss portions of the media due to the interruption (e.g., the obscuration due to another occupant, an object, etc.).

In various embodiments, the control module 102 may again control the projector module 104 to project the visual media for the occupant. For example, in response to detecting the occupant looking again at the projector module 104 after the interruption (e.g., the obscuration is no longer present), the control module 102 may control the projector module 104 to reinitiate the projecting of the visual media for the occupant. In some examples, the control module 102 may control the projector module 104 to reinitiate the projecting at a point of interruption in the visual media (e.g., at a point when the media was paused). In other examples, the control module 102 may control the projector module 104 to reinitiate the projecting of the media in real time as if the media was not paused.

In some embodiments, the control module 102 may detect the duration of the interruption and then continue the projection from when the original blocking occurred to when the blockage ended. For example, in response to detecting the interruption, the control module 102 may initiate a timer. Once the control module 102 detects the occupant looking again at the projector module 104 (e.g., the obscuration is no longer present), the control module 102 may determine a period of time based on the timer between detecting the initial interruption and detecting the occupant looking again at the projector module after the interruption.

Then, the control module 102 may take different courses of action based on the determined period of time. For example, the control module 102 may compare the determined period of time to a defined threshold. If the determined period of time is greater than the defined threshold, the control module 102 may control the projector module 104 to pause projecting of the visual media for the occupant and then reinitiate the projecting at a point of interruption. If, however, the determined period of time is less than the defined threshold, the control module 102 may control the projector module 104 to pause projecting of the visual media for the occupant and reinitiate the projecting of the media in real time as if the media was not paused. Alternatively, the projector module 104 may not pause projecting if the determined period of time is less than the defined threshold.

The defined threshold may be any suitable period of time. For example, the defined threshold may be any suitable time from 10 milliseconds to 100 milliseconds. In various embodiments, the threshold may depend on the type of media being presented. In such examples, if the projected media is a movie, an advertisement, etc., the period of time may be short (e.g., representing a momentarily brief interruption). If, however, the projected media is a map, a user selected feature (e.g., advertisement, movie, program, etc.), the period of time may be longer. In other examples, the threshold may be based on a frame rate of the projected media. For example, if the frame rate is 60 frames/second, the threshold may be at least 15 milliseconds.

In various embodiments, the control module 102 may generate an alert for the occupant if an interruption has occurred. For example, after the interruption is detected (e.g., in response to detecting the interruption, a period of time after detecting the interruption, etc.), the control module 102 may transmit a control signal to the alert generator 114. In response, the alert generator 114 may activate one or more alerts to notify one or more occupants in the vehicle of an interruption. For example, the alert generator 114 may generate a visual alert, generate an audible alert (e.g., a voice command), generate a haptic alert, etc.

Figure 6:
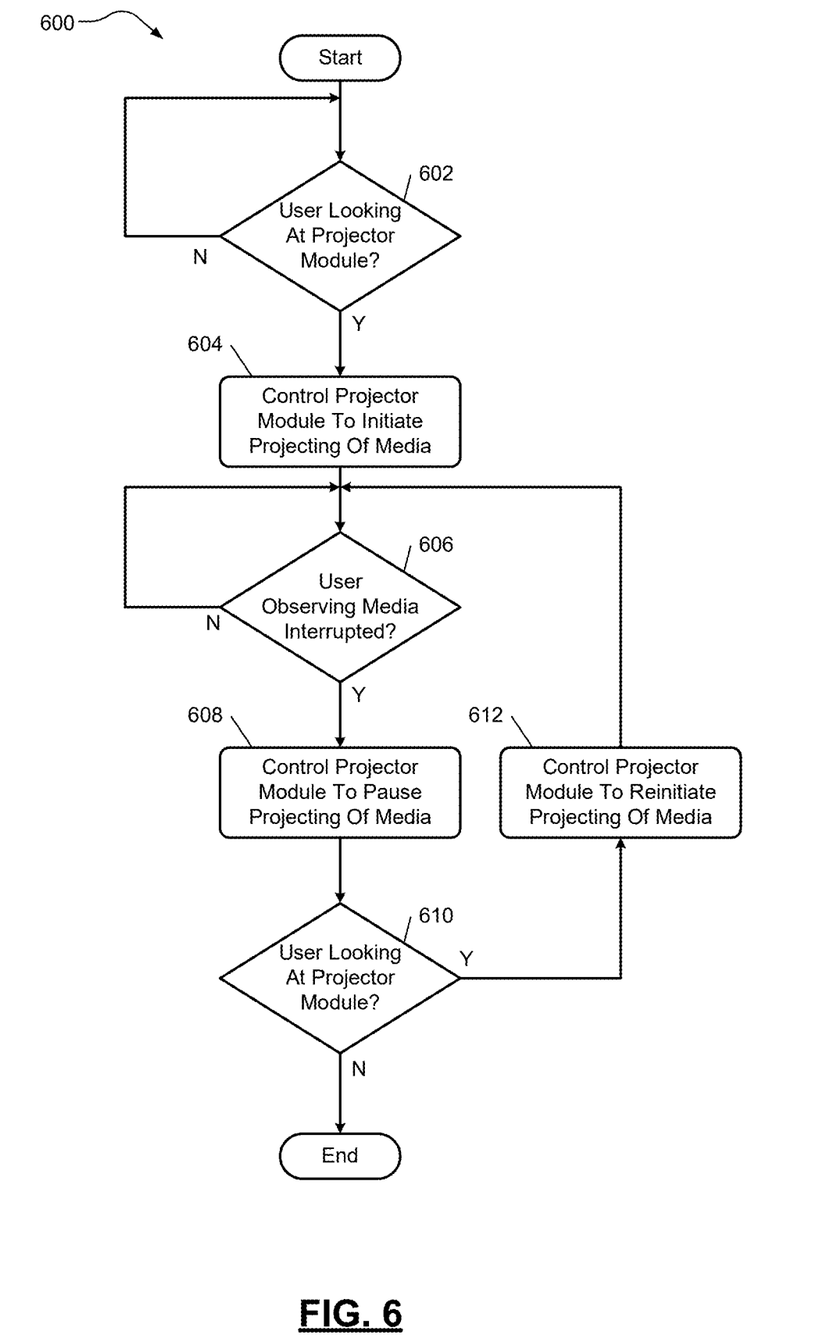
FIGS. 6-7 are flowcharts of example control processes for controlling projection of visual media for occupants, according to the present disclosure.
Figure 7:
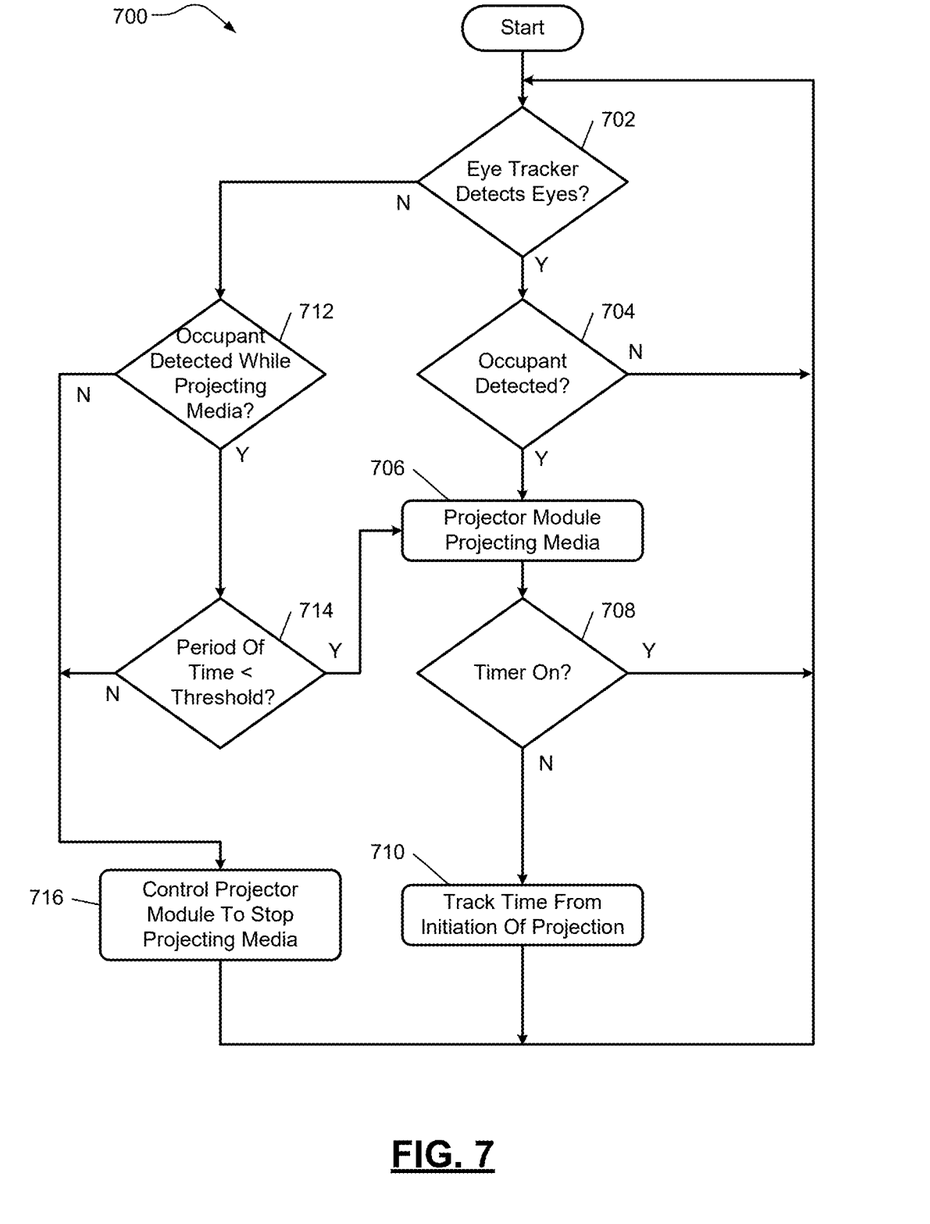

FIGS. 6-7 illustrate example control processes 600, 700 employable by the system 100 of FIG. 1 for controlling projection of visual media for occupants in vehicles (e.g., the vehicle 200 of FIG. 2). Although the example control processes 600, 700 are described in relation to the system 100 of FIG. 1 including the control module 102, any one of the control processes 600, 700 may be employable by any suitable system.

In FIG. 6, the control process 600 begins at 602, where the control module 102 detects whether a user (e.g., an occupant, a passenger, etc.) is looking at a projector module (e.g., the projector module 104). In various embodiments, the control module 102 may make this determination based on one or more signals from one or more user tracking sensors, such as the face tracker sensor 110, the eye tracker sensor 112, etc. of FIG. 1 as explained above. If no at 602, control returns to 602. If yes, control proceeds to 604.

At 604, the control module 102 controls the projector module to initiate projecting of visual media for the user. For example, and as explained above, the control module 102 may generate and transmit a control signal to the projector module, thereby instructing the projector module to project the visual media. Control then proceeds to 606.

At 606, the control module 102 determines whether an interruption occurs with the user observing the visual media. In various embodiments, the control module 102 may make this determination based on one or more signals from the face tracker sensor 110, the eye tracker sensor 112, etc. of FIG. 1 as explained above. If no, control returns to 606 where the projector module continues projecting of the visual media for the user. If yes, control proceeds to 608.

At 608, the control module 102 controls the projector module to pause projecting of the visual media. For example, and as explained above, such control may be accomplished by generating and transmitting a control signal to the projector module, thereby instructing the projector module to pause. Control then proceeds to 610.

At 610, the control module 102 detects whether the user is again looking at the projector module based on, for example, the face tracker sensor 110, the eye tracker sensor 112, etc. of FIG. 1. If yes, control proceeds to 612 where the control module 102 controls the projector module to reinitiate projecting of the visual media for the user as explained above. Control then returns to 606.

If no at 610, control may end as shown in FIG. 6. For example, control may end after a defined period of time of no user eye engagement (e.g., an interruption time exceeds a threshold). In other examples, control may end after a defined number of attempts to detect whether the user is again looking at the projector module, etc. In such examples, control may return to 610 a defined number of times before ending.

In FIG. 7, the control process 700 begins at 702, where the control module 102 detects whether a user (e.g., an occupant, a passenger, etc.) is looking at a projector module (e.g., the projector module 104). For example, and as explained above, the control module 102 may make this determination based on the face tracker sensor 110, the eye tracker sensor 112, etc. of FIG. 1. If yes at 702, control proceeds to 704. If no, control proceeds to 712.

At 704, the control module 102 determines whether the user is detected. For example, the control module 102 may receive one or more signals with sensed parameter(s) from one or more occupancy detection sensors, such as the occupant classification sensor 106, the biometric sensor 108, etc. of FIG. 1, and then detect whether a seat is occupied by an object indicative of an individual based on the sensed parameter. If no at 704, control returns to 702. If yes, control proceeds to 706 where the control module 102 controls the projector module to project visual media for the user, as explained above. Control then proceeds to 708.

At 708, the control module 102 determines whether a timer was previously set (e.g., turned on, initiated, etc.). If yes, control returns to 702. If no, proceeds to 710 where the control module 102 initiates a timer to track a time from the initiation of the projected media. Control then returns to 702.

At 712, the control module 102 determines whether the user is detected based on, for example, one or more occupancy detection sensors (e.g., as explained above) while the projector module is projecting the visual media. If yes at 712, control proceeds to 714 where the control module 102 determines whether a period of time corresponding to an interruption (e.g., when the user is not looking at the projector module determined at 702) is less than a defined threshold. If yes at 714, control returns to 706 where the control module 102 controls the projector module to project visual media for the user, as explained above. If no at 714, control proceeds to 716. If no at 712, control proceeds to 716 where the control module 102 controls the projector module to pause or stop projecting of the visual media, as explained above. Control then returns to 702. In such examples, the control module 102 may control the projector module to reinitiate the projecting of the visual media at a point of interruption (as explained above) if the control module 102 detects the user is looking again at the projector module (at 702) and determines the user is an occupant of the seat (at 704).

The foregoing description is merely illustrative in nature and is in no way intended to limit the disclosure, its application, or uses. The broad teachings of the disclosure can be implemented in a variety of forms. Therefore, while this disclosure includes particular examples, the true scope of the disclosure should not be so limited since other modifications will become apparent upon a study of the drawings, the specification, and the following claims. It should be understood that one or more steps within a method may be executed in different order (or concurrently) without altering the principles of the present disclosure. Further, although each of the embodiments is described above as having certain features, any one or more of those features described with respect to any embodiment of the disclosure can be implemented in and/or combined with features of any of the other embodiments, even if that combination is not explicitly described. In other words, the described embodiments are not mutually exclusive, and permutations of one or more embodiments with one another remain within the scope of this disclosure.

Spatial and functional relationships between elements (for example, between modules, circuit elements, semiconductor layers, etc.) are described using various terms, including "connected," "engaged," "coupled," "adjacent," "next to," "on top of," "above," "below," and "disposed." Unless explicitly described as being "direct," when a relationship between first and second elements is described in the above disclosure, that relationship can be a direct relationship where no other intervening elements are present between the first and second elements, but can also be an indirect relationship where one or more intervening elements are present (either spatially or functionally) between the first and second elements. As used herein, the phrase at least one of A, B, and C should be construed to mean a logical (A OR B OR C), using a non-exclusive logical OR, and should not be construed to mean "at least one of A, at least one of B, and at least one of C."

In the figures, the direction of an arrow, as indicated by the arrowhead, generally demonstrates the flow of information (such as data or instructions) that is of interest to the illustration. For example, when element A and element B exchange a variety of information but information transmitted from element A to element B is relevant to the illustration, the arrow may point from element A to element B. This unidirectional arrow does not imply that no other information is transmitted from element B to element A. Further, for information sent from element A to element B, element B may send requests for, or receipt acknowledgements of, the information to element A.

In this application, including the definitions below, the term "module" or the term "controller" may be replaced with the term "circuit." The term "module" may refer to, be part of, or include: an Application Specific Integrated Circuit (ASIC); a digital, analog, or mixed analog/digital discrete circuit; a digital, analog, or mixed analog/digital integrated circuit; a combinational logic circuit; a field programmable gate array (FPGA); a processor circuit (shared, dedicated, or group) that executes code; a memory circuit (shared, dedicated, or group) that stores code executed by the processor circuit; other suitable hardware components that provide the described functionality; or a combination of some or all of the above, such as in a system-on-chip.

The module may include one or more interface circuits. In some examples, the interface circuits may include wired or wireless interfaces that are connected to a local area network (LAN), the Internet, a wide area network (WAN), or combinations thereof. The functionality of any given module of the present disclosure may be distributed among multiple modules that are connected via interface circuits. For example, multiple modules may allow load balancing. In a further example, a server (also known as remote, or cloud) module may accomplish some functionality on behalf of a client module.

The term code, as used above, may include software, firmware, and/or microcode, and may refer to programs, routines, functions, classes, data structures, and/or objects. The term shared processor circuit encompasses a single processor circuit that executes some or all code from multiple modules. The term group processor circuit encompasses a processor circuit that, in combination with additional processor circuits, executes some or all code from one or more modules. References to multiple processor circuits encompass multiple processor circuits on discrete dies, multiple processor circuits on a single die, multiple cores of a single processor circuit, multiple threads of a single processor circuit, or a combination of the above. The term shared memory circuit encompasses a single memory circuit that stores some or all code from multiple modules. The term group memory circuit encompasses a memory circuit that, in combination with additional memories, stores some or all code from one or more modules.

The term memory circuit is a subset of the term computer-readable medium. The term computer-readable medium, as used herein, does not encompass transitory electrical or electromagnetic signals propagating through a medium (such as on a carrier wave); the term computer-readable medium may therefore be considered tangible and non-transitory. Non-limiting examples of a non-transitory, tangible computer-readable medium are nonvolatile memory circuits (such as a flash memory circuit, an erasable programmable read-only memory circuit, or a mask read-only memory circuit), volatile memory circuits (such as a static random access memory circuit or a dynamic random access memory circuit), magnetic storage media (such as an analog or digital magnetic tape or a hard disk drive), and optical storage media (such as a CD, a DVD, or a Blu-ray Disc).

The apparatuses and methods described in this application may be partially or fully implemented by a special purpose computer created by configuring a general purpose computer to execute one or more particular functions embodied in computer programs. The functional blocks, flowchart components, and other elements described above serve as software specifications, which can be translated into the computer programs by the routine work of a skilled technician or programmer.

The computer programs include processor-executable instructions that are stored on at least one non-transitory, tangible computer-readable medium. The computer programs may also include or rely on stored data. The computer programs may encompass a basic input/output system (BIOS) that interacts with hardware of the special purpose computer, device drivers that interact with particular devices of the special purpose computer, one or more operating systems, user applications, background services, background applications, etc.

The computer programs may include: (i) descriptive text to be parsed, such as HTML (hypertext markup language), XML (extensible markup language), or JSON (JavaScript Object Notation) (ii) assembly code, (iii) object code generated from source code by a compiler, (iv) source code for execution by an interpreter, (v) source code for compilation and execution by a just-in-time compiler, etc. As examples only, source code may be written using syntax from languages including C, C++, C#, Objective-C, Swift, Haskell, Go, SQL, R, Lisp, Java®, Fortran, Perl, Pascal, Curl, OCaml, Javascript®, HTML5 (Hypertext Markup Language 5th revision), Ada, ASP (Active Server Pages), PHP (PHP: Hypertext Preprocessor), Scala, Eiffel, Smalltalk, Erlang, Ruby, Flash®, Visual Basic®, Lua, MATLAB, SIMULINK, and Python®.

What is claimed is:

1. A system for controlling projection of a visual media for a user in a vehicle, the system comprising:
   a projector module configured to project a visual media for a user in the vehicle;
   a user tracking sensor configured to sense whether the user is observing the visual media; and
   a control module in communication with the projector module and the user tracking sensor, the control module configured to:
   detect whether the user is looking at the projector module based on a first signal from the user tracking sensor;
   in response to detecting the user is looking at the projector module, control the projector module to initiate projecting of the visual media for the user;
   detect an interruption of the user observing the visual media based on a second signal from the user tracking sensor;
   detect the user looking again at the projector module after the interruption;
   determine a period of time between detecting the interruption of the user observing the visual media and detecting the user looking again at the projector module after the interruption; and
   in response to detecting the interruption of the user observing the visual media, control the projector module to pause projecting of the visual media for the user only if the period of time is greater than a defined threshold.

2. The system of claim 1, wherein the user tracking sensor includes at least one of an eye tracking sensor and a face tracking sensor.

3. The system of claim 1, further comprising an occupancy detection sensor configured to sense a parameter associated with a seat in the vehicle, wherein:
   the control module is in communication with the occupancy detection sensor; and
   the control module is configured to detect whether the seat is occupied by an object indicative of an individual based on the sensed parameter, and control the projector module to initiate projecting of the visual media for the user in response to detecting that the seat is occupied by the object indicative of the individual.

4. The system of claim 3, wherein the occupancy detection sensor includes at least one of a biometric sensor positioned in the seat and a weight sensor positioned in the seat.

5. The system of claim 1, wherein the projector module includes a retinal projector module configured to project the visual media directly into retinas of the user in the vehicle.

6. The system of claim 1, wherein the control module is configured to generate an alert for the user in response to detecting the interruption.

7. The system of claim 6, wherein the alert includes at least one of an audible alert and a haptic alert.

8. The system of claim 1, wherein the control module is configured to detect the user looking again at the projector module after the interruption and control the projector module to reinitiate the projecting of the visual media for the user in response to detecting the user looking again at the projector module after the interruption.

9. The system of claim 8, wherein the control module is configured to control the projector module to reinitiate the projecting of the visual media at a point of interruption in the visual media.

10. A vehicle comprising the system of claim 1, a first seat, and a second seat opposing the first seat, wherein the projector module is positioned in the first seat and configured to project the visual media towards the second seat.

11. The vehicle of claim 10, wherein the user tracking sensor is positioned in the first seat and coaligned with the projector module.

12. A method for controlling projection of a visual media for a user in a vehicle, the method comprising:
   detecting whether a seat is occupied by an object indicative of an individual based on a sensed parameter received from an occupancy detection sensor;
   detecting whether the user is looking at a projector module based on a first signal received from a user tracking sensor;
   in response to detecting that the seat is occupied by the object indicative of the individual and detecting the user is looking at the projector module, controlling the projector module to initiate projecting of the visual media for the user;
   detecting an interruption of the user observing the visual media based on a second signal from the user tracking sensor; and
   in response to detecting the interruption of the user observing the visual media, controlling the projector module to pause projecting of the visual media for the user.

13. The method of claim 12, wherein:
   the user tracking sensor includes at least one of an eye tracking sensor and a face tracking sensor; and
   the occupancy detection sensor includes at least one of a biometric sensor positioned in the seat and a weight sensor positioned in the seat.

14. The method of claim 12, further comprising generating an alert for the user in response to detecting the interruption.

15. The method of claim 14, wherein the alert includes at least one of an audible alert and a haptic alert.

16. The method of claim 12, further comprising:
   detecting the user looking again at the projector module after the interruption; and
   controlling the projector module to reinitiate the projecting of the visual media for the user in response to detecting the user looking again at the projector module after the interruption.

17. The method of claim 16, wherein controlling the projector module to reinitiate the projecting of the visual media for the user includes controlling the projector module to reinitiate the projecting of the visual media at a point of interruption in the visual media.

18. The method of claim 12, wherein:
   the method further comprises detecting the user looking again at the projector module after the interruption, and determining a period of time between detecting the interruption of the user observing the visual media and detecting the user looking again at the projector module after the interruption; and
   controlling the projector module to pause projecting of the visual media includes controlling the projector module to pause projecting of the visual media only if the period of time is greater than a defined threshold.

19. A system for controlling projection of a visual media for a user in a vehicle, the system comprising:
   an occupancy detection sensor configured to sense a parameter associated with a seat in the vehicle;
   a projector module configured to project a visual media for a user in the vehicle;
   a user tracking sensor configured to sense whether the user is observing the visual media; and
   a control module in communication with the occupancy detection sensor, the projector module and the user tracking sensor, the control module configured to:
      detect whether the seat is occupied by an object indicative of an individual based on the sensed parameter;
      detect whether the user is looking at the projector module based on a first signal from the user tracking sensor;
      in response to detecting that the seat is occupied by the object indicative of the individual and detecting the user is looking at the projector module, control the projector module to initiate projecting of the visual media for the user;
      detect an interruption of the user observing the visual media based on a second signal from the user tracking sensor; and
      in response to detecting the interruption of the user observing the visual media, control the projector module to pause projecting of the visual media for the user.

20. The system of claim 19, wherein the occupancy detection sensor includes at least one of a biometric sensor positioned in the seat and a weight sensor positioned in the seat.

* * * * *